(12) United States Patent
Weiss

(10) Patent No.: US 6,338,950 B2
(45) Date of Patent: *Jan. 15, 2002

(54) DNA ENCODING LST-1 PROTEIN AND PROCESS FOR RECOMBINANT PRODUCTION OF LST-1 PROTEIN

(75) Inventor: Elisabeth Weiss, München (DE)

(73) Assignee: Roche Diagnostics GmbH, Mannheim (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,544
(22) PCT Filed: Jun. 20, 1996
(86) PCT No.: PCT/EP96/02663
　§ 371 Date: Dec. 18, 1997
　§ 102(e) Date: Dec. 18, 1997
(87) PCT Pub. No.: WO97/00950
　PCT Pub. Date: Jan. 9, 1997

(30) Foreign Application Priority Data

Jun. 20, 1995 (EP) .............................. 95109511
Aug. 3, 1995 (EP) .............................. 95112201

(51) Int. Cl.[7] .................. C12N 15/12; C07H 21/04
(52) U.S. Cl. .................. 435/69.1; 435/325; 435/252.3; 435/252.33; 435/320.1; 536/23.5
(58) Field of Search ................ 536/23.5; 435/69.1, 435/69.7, 325, 252.3, 320.1, 252.33

(56) References Cited

FOREIGN PATENT DOCUMENTS

EP　　0 315 950　　5/1989
WO　　94/01548　　* 1/1994

OTHER PUBLICATIONS

G.E. Nedwin et al., Nucleic Acids Research 13(17):6361–6373 (1985) Human lymphotoxin and tumor necrosis factor genes: structure, homology and chromosomal localization.*

J.M. Iris et al., Nature Genetics 3:137–145, Feb. 1993. Dense Alu clustering and a potential new member of the NFκB family within a 90 kilobase HLA Class III segment.*

I. Holzinger et al., Genbank locus HSLST1G, Direct sequence submission Aug. 26, 1992, Accessed Mar. 27, 1999.*

L. J. Abraham et al., European Journal of Immunogenetics 19:165–168, 1992, Polymorphism in the Human B144 gene in different MHC haplotypes.*

L. Hillier et al, Genbank locus R71126, Jun. 1, 1995, Accessed Mar. 27, 1999.*

L. Hillier et al, Genbank locus T79306, Mar. 15, 1995, Accessed Mar. 27, 1999.*

L. Hillier et al, Genbank locus T79220, Mar. 15, 1995, Accessed Mar. 27, 1999.*

EMBL Primate Databank, Accession No. u00921.

EMBL Primate Databank, Accession No. X67841.

International Publication No. WO 87/06942 published Nov. 19, 1987.

International Publication No. WO 90/1330 published Nov. 15, 1990.

Hum Immunol, Jan. 1995, 42 (1) p9–14, DeBaey et al., "Pvu II polymorphism in the primate homologue of the mouse B144 (LST–1) . . . ".

Immunobiology, 191 (2–3). 1994. 149., Holzinger I et al., "LST–1, a novel gene in the human TNF region." –Abstract Only.

* cited by examiner

*Primary Examiner*—Lorraine Spector
(74) *Attorney, Agent, or Firm*—George W. Johnston; Dennis P. Tramaloni; F. Aaron Dubberley

(57) ABSTRACT

The invention concerns a new immunoregulatory protein LST-1, nucleic acd sequences coding for this protein, a process for the isolation of this protein, as well as its use for the production of a therapeutic agent. The DNA and protein sequences are shown in SEQ ID NO:1 to 4.

6 Claims, No Drawings

DNA ENCODING LST-1 PROTEIN AND PROCESS FOR RECOMBINANT PRODUCTION OF LST-1 PROTEIN

This invention relates to a new leukocyte specific and immunoregulatory protein (LST-1) and to the corresponding protein produced by recombinant techniques as well as nucleic acids which code for proteins with LST-1 activity, methods of use and of production.

Cytokines are proteins with a molecular weight of less than 50 kD, which mediate the exchange of autocrine, paracrine or endocrine signals between the cellular components of tissues or between different tissues. The cytokines identified so far include growth factors, interleukins and interferons and act on cells in many systems of the body: the hematopoietic system, the immune system, the nervous system, the skeletal system, connective tissues, and probably most other tissues and organs of the body (for reference see A. Thompson ed. (1991), The Cytokine Handbook, London, Academic Press and A. Miyajima et al., Annual Reviews Immunol. 10 (1992) 295–331). Examples of cytokines are EGF, NGF, PDGF, FGF, IL-1 to IL-7, GM-CSF, G-CSF, MCSF, IFN, TNF-$\alpha$, TG-$\alpha$ and -$\beta$.

More than 100 cytokines have been identified so far, but there is a need for further new cytokines which might be important for potential health care advances.

SUMMARY OF THE INVENTION

Accordingly it is an object of the present invention to provide a new cytokine showing new biological properties.

It is a further object of the present invention to provide the new protein using recombinant DNA molecules capable of expressing said protein in order that the binding protein will be more readily available. These and other objects of the invention have been accomplished by providing a purified protein according to the invention, selected from a group consisting of a protein which is at least 85% homologous to the amino acid sequence SEQ ID NO:3 and fragments thereof, wherein said protein is capable of binding to an antibody specific for said protein or its cell surface receptor on leukocytes.

DESCRIPTION OF SPECIFIC EMBODIMENTS

The invention comprises especially novel therapeutic compositions comprising recombinant proteins produced using nucleic acid sequences encoding proteins with LST-1 activity. The LST-1 cDNA which can be used for the production of the recombinant protein was initially isolated from U-937 cells (DSM ACC 5) stimulated with IFN-$\gamma$. RT-PCR cloning of mMRA from these cells resulted in a cDNA clone designated pLST-1 having a length of 636 bp. Analysis of the LST-1 cDNA reveals that LST-1 consists of six exons. These exons are designated SEQ ID NO:1 exons 1A (bp 48–162), 1B (bp 544–652), 2 (bp 1044–1162), 3 (bp 1475–1567), 4 (bp 1775–1797) and 5 (bp-2325–2709). In SEQ ID NO:2 exon 5, after position 2345, there is an internal 5' donor splice site. By alternative splicing, thus, two isoforms of the LST-1 protein can be formed, which accordingly have a length of either 104 or 97 amino acids (cf. SEQ ID NOS: 3 and 4). The human pLST-1 cDNA done contains an extended 5' region encoding stop codons.

The invention is based on a new cytokine-like protein (denoted LST-1 protein, or LST-1, in the following) whose production is stimulated in U-937 cells by IFN-$\gamma$ by a factor of more than 100 preferably 1000, which binds to the surface of leukocytes and which a) is coded by the DNA sequence shown in SEQ ID NO:2 for the mature protein or by the genomic sequence shown in SEQ ID NO:1, b) is coded by DNA sequences which hybridize under stringent conditions with the DNA sequences shown in SEQ ID NO:1 or 2 or fragments of the DNA sequences in the DNA region which codes for the mature protein, or c) is coded by DNA sequences which, if there was no degeneracy of the genetic code, would hybridize with the sequences defined in a) or b) and code for a polypeptide with amino acid sequence, d) and the reading frame of said protein is defined by ATG starting at position 1144 of SEQ ID NO:1 following within no shift of the reading frame in the protein coding region following said ATG.

The protein can be defined by its DNA sequence (preferably by its cDNA sequence deduced from SEQ ID NO:1) and by the amino acid sequence derived therefrom. The LST-1 protein can occur in natural allelic variations which differ from individual to individual. Such variations of the amino acids are usually amino acid substitutions. However, they may also be deletions, insertions or additions of amino acids to the total sequence. The LST-1 protein according to the invention—depending, both in respect of the extent and type, on the cell and cell type in which it is expressed—can be in glycosylated or non-glycosylated form The LST-1 proteins according to SEQ ID NO:3 and SEQ ID NO:4 are preferred.

LST-1 mRNA is expressed constitutively in T cells, macrophages, U-937 and at low levels in human tonsilla, lung and liver, which may be due to the lymphocytes and macrophages present in these tissues the protein shows an immunoregulatory activity. Transcription can be strongly enhanced by IFN-$\gamma$ in U-937 cells. Upon stimulation of the Jurkat T cell line (ATCC TIB 152) with TPA (12-o-tetradecanoylphorbol-13-acetate) only a short induction of LST-1 mRNA was observed. An increase of mRNA expression starts after four hours with a peak after 8 hours of stimulation and further decrease after 24 hours of stimulation.

"Immunoregulatory activity" means that the protein modulates directly or non-directly the cooperation of T-cells with macrophages.

The binding to the surface of leucocytes is preferably estimated in vitro. Such methods are known in the state of the art.

The term "hybridize under stringent conditions" means that two nucleic acid fragments are capable of hybridization to one another under standard hybridization conditions described in Sambrook et al., "Expression of cloned genes in E. coli" in Molecular Cloning: A laboratory manual (1989) Cold Spring Harbor Laboratory Press, New York, USA, 9.47–9.62 and 11.45–11.61.

More specifically, stringent conditions as used herein refer to hybridization in 1 mol/l NaCl 1% SDS and 10% dextransulfate. This is followed by two washes of the filter at room temperature of 5 minutes in 2×SSC and one final wash for 30 minutes. This final wash may be at 0.5×SSC, 0.1% SDS, more preferably at 0.2×SSC, 0.1% SDS and most preferably at 0.1×SSC, 0.1% SDS, final wash taking place at 65° C. Those of ordinary skilled in the art will recognize to that other conditions will afford the same degrees of stringency and are encompassed by the phraseology "under stringent conditions" and are encompassed herein.

LST-1 is a protein which is active in its glycosylated or unglycosylated form. The unglycosylated form can be produced by recombinant technology in prokaryotic cells.

"Proteins with LST-1 activity" means also proteins with minor amino acid variations but with substantially the same LST1 activity. Substantially the same means that the activities are of the same biological properties and preferably at least 85% homology in amino acid sequence. More preferably, the amino acid sequences are at least 90% identical. LST-1 can be purified from U-937 cells by affinity chromatography using a monoclonal antibody against LST-1. It is also preferred to use other known protein purification techniques, including immunoprecipitation, gel filtration, ion exchange, chromatography, chromatofocussing, isoelectric focussing, selective precipitation, electrophoresis, and the like. Fraction isolated during purification procedures can be analyzed for the presence of LST-1 activity by using LST-1 specific antibodies.

The protein according to the invention can also be produced by recombinant means. Non-glycosylated LST-1 protein is obtained when it is produced recombinantly in prokaryotes. With the aid of the nucleic acid sequences provided by the invention it is possible to search for the LST-1 gene or its variants in genomes of any desired cells (e.g. apart from human cells, also in cells of other mammals), to identify these and to isolate the desired gene coding for the LST-1 protein Such processes and suitable hybridization conditions are known to a person skilled in the art and are described, for example, by Sambrook, J., et al., "Expression of cloned genes in *E. coli*" in Molecular Cloning: A laboratory manual (1989) Cold Spring Harbor Laboratory Press, New York, USA, and B. D. Hames, S. G. Higgins, Nucleic acid hybridisation—a practical approach (1985) IRL Press, Oxford, England. In this case the standard protocols described in these publications are usually used for the experiments.

The use of recombinant DNA technology enables the production of numerous LST-1 protein derivatives. Such derivatives can, for example, be modified in individual or several amino acids by substitution, deletion or addition. The derivatization can, for example, be carried out by means of site directed mtutagenesis. Such variations can be easily carried out by a person skilled in the art (J. Sambrook, B. D. Hames, loc. cit.). It merely has to be ensured that the characteristic properties of the LST-1 protein (inhibition of the aforementioned cell lines) are preserved. The invention therefore in addition concerns a LST-1 protein which is a product of a prokaryotic or eukaryotic expression of an exogenous DNA.

The invention concerns a nucleic acid molecule for use in securing expression in a prokaryotic or eukaryotic host cell of a LST-1 protein and is selected from the group comprising
   a) DNA sequences shown in SEQ ID NO:1 and 2 or the complementary sequences,
   b) nucleic acid sequences which hybridize under stringent conditions with one of the sequences from a),
   c) nucleic acid sequences which, if there was no degeneracy of the genetic code, would hybridize with one of the sequences stated in a) or b),
   d) and the reading frame of said protein is defined by ATG starting at position 1144 of SEQ ID NO:1 following within no shift of the reading frame in the protein coding region following said ATG.

With the aid of such nucleic acids coding for a LST-1 protein, the protein according to the invention can be obtained in a reproducible manner and in large amounts. For expression in prokaryotic or eukaryotic organisms, such as prokaryotic host cells or eukaryotic host cells, the nucleic acid is integrated into suitable expression vectors, according to methods familiar to a person skilled in the arm Such an expression vector preferably contains a regulatable/inducible promoter. These recombinant vectors are then introduced for the expression into suitable host cells such as, e.g., *E. coli* as a prokaryotic host cell or Saccharomyces cerevisiae, Terato carcinoma cell line PA-1 sc 9117 (Büttner et al., Mol. Cell. Biol. 11 (1991) 3573–3583), insect cells, CHO or COS cells as eukaryotic host cells and the transformed or transduced host cells are cultured under conditions which allow an expression of the heterologous gene. The isolation of the protein can be carried out according to known methods from the host cell or from the culture supernatant of the host cell. Such methods are described for example by Ausubel I., Frederick M., Current Protocols in Mol. Biol. (1992), John Wiley and Sons, New York. Also in vitro reactivation of the protein may be necessary.

In addition the invention concerns a process for obtaining a LST-1 protein by isolation of the culture supernatant of the U-937 cell line by means of a gel chromatographic separation and purification of a fraction.

The detection of transformed or transduced host cells which recombinantly produce the LST-1 protein and the purification of the protein are preferably carried out by means of antibodies which bind to this protein. Such antibodies can be obtained in a simple manner according to known methods by using the protein according to the invention as an antigen or an immunogen.

The invention therefore in addition concerns the use of the protein with LST-1 activity according to the invention for the production of antibodies which bind to this protein.

Anti-LST-1 antibodies are produced by immunization on and appropriate vertebrate host with purified LST-1 or polypeptide derivatives of LST-1, preferably with an adjuvant. Said techniques are well-known in the literature and are described, for example, by Harlow and Lane eds., Antibodies: A laboratory manual (1988), Cold Spring Harbor Laboratories Press.

For this, animals which are usually used for this purpose, such as in particular, sheep, rabbits or mice, are immunized with the protein according to the invention and subsequently the antiserum is isolated from the immunized animals according to known methods or spleen cells of the immunized animals are fused with immortalized cells, such as e.g. myeloma cells, according to the method of Köhler and Milstein (Nature 256 (1975) 495–497). Those cells which produce a monoclonal antibody at the LST-1 protein are selected from the hybridoma cells obtained in this way and cloned. The monoclonal or polyclonal antibodies obtained in this way can be bound to a support material, such as e.g. cellulose, for an imunoabsorptive purification of the melanoma—inhibiting protein Furthermore, antibodies of this kind can be used for the detection of the LST-1 protein in samples, such as e.g. cut tissue or body fluids.

The invention therefore additionally concerns antibodies against the LST-1 protein which are obtainable by immunizing an animal with a LST-1 protein and isolating the antibodies from the serum or spleen cells of the immunized animals.

It has in addition turned out that the LST-1 protein has an immunoregulatory activity.

The invention in addition concerns the use of a protein according to the invention for the production of a therapeutic agent which can be used in tumor therapy or as an immunoregulating agent The protein according to the invention is processed, if desired together with the usually used auxiliary agents, fillers and/or additives, in a pharmaceutical formulation for the said therapeutic applications.

The invention therefore in addition concerns a therapeutic composition containing a LST-1 protein according to the invention and if desired together with the auxiliary agents, fillers and/or additives that are usually used.

The invention further concerns the use of sequences of the LST-1 gene, preferably nucleic acid molecules coding for a protein having LST-1 activity, or activating polynucleotides from the 5' untranslated region, in gene therapy, and in particular, for the production of medicaments for gene therapy.

Gene therapy of somatic cells can be accomplished by using, e.g., retroviral vectors, other viral vectors, or by non-viral gene transfer (for clarity cf. T. Friedmann, Science 244 (1989) 1275; Morgan 1993, RAC DATA MANAGEMENT REPORT, June 1993).

Vector systems suitable for gene therapy are, for instance, retroviruses (Mulligan, R. C. (1991) in Nobel Symposium 8: Ethiology of human disease at the DNA level (Lindsten, J. and Pattersun Editors) 143–189, Raven Press), adeno associated virus (McLughlin, J. Virol. 62 (1988), 1963), vaccinia virus (Moss et al., Ann. Rev. Immunol. 5 (1987) 305), bovine papilloma virus (Rasmussen et al., Methods Enzymol. 139 (1987) 642) or viruses from the group of the herpes viruses such as Epstein Barr virus (Margolskee et al., Mol. Cell. Biol. 8 (1988) 2937) or herpes simplex virus.

There are also known non-viral delivery systems. For this, usually "nude" nucleic acid, preferably DNA, is used, or nucleic acid together with an auxilary such as, e.g., transfer reagents (liposomes, dendromers, polylysine-transferrine-conjugates (Felgner et al., Proc. Natl. Acad. Sci. USA 84 (1987) 7413).

Another preferred method of gene therapy is based on homologous recombination. In this, either the gene coding for the LST-1 protein can be inserted in one or more copies into the genome of somatic cells and/or the LST-1 gene endogenously present in the cells can be modulated, preferably activated.

Methods of homologous recombination are described, e.g., in Kucherlapati, Proc. in Nucl. Acids Res. and Mol. Biol. 36 (1989) 301; Thomas et al., Cell 44 (1986) 419–428; Thomas and Capecchi, Cell 51 (1987) 503–512; Doetschman et al., Proc. Natd. Acad. Sci. USA 85 (1988) 8583–8587 and Doetschman et al., Nature 330 (1987) 576–578. In these methods, a portion of DNA to be integrated at a specific site in the genome (gene fragment of LST-1) is bound to a targeting DNA. The targeting DNA is a DNA which is complementary (homologous) to a region (preferably within or proximal to the LST-1 gene) of the genomic DNA When two homologous portions of a single-stranded DNA (e.g. the targeting DNA and the genomic DNA) are in close proximity to one another they will hybridize and form a double-stranded helix. Then the LST-1 gene fragment and the targeting DNA can be integrated into the genome by means of occurrence of recombination. This homologous recombination can be carried out both in vitro and in vivo (in the patient).

Preferably, there is used a DNA which codes for a protein having LST-1 activity, a fragment which inhibits LST-1 expression (knock-out sequence) or a fragment capable of activating, after integration of the genome of a cell, expression, in this cell, of a protein having LST-1 activity. Such a fragment may be, for example, a promoter and/or enhancer region which is heterologous to the corresponding LST-1 region or which, after integration into the LST-1 gene, activates the actually silent or to a little extent expressed LST-1 gene transcriptionally and/or translationally.

Thus, by means of this DNA, one or more LST-1 genes are newly introduced into the target cell, or the essentially transcriptionally silent gene in the genome of a mamma cell is activated in such fashion that the mammalian cell is enabled to produce endogenous LST-1 protein. To this end, a DNA construct is inserted into the genome by homologous recombination, the DNA construct comprising the following: a DNA regulatory element capable of stimulating expression of this gene if operatively linked thereto; and one or more DNA target segments which are homologous to a region in this genome, which region is within or proximal to this gene. This construct is inserted into the genome of the mammalian cell in such fashion that the regulatory segment is operatively linked to the gene which codes for the protein having LST-1 activity. Preferably, the construct further comprises amplifying sequences, especially if genes coding for proteins with LST-1 activity are inserted into the cell.

For the introduction of LST-1 genes into the target cells, the construct comprises a regulatory element, one or more LST-1 genes and one or more target segments. The target segments are chosen in such a way that they hybridize with an appropriate region of the genome, whereby, after homologous recombination, the inserted exogenous LST-1 genes are expressed.

There are known a large number of processes by which homologous recombination can be initiated. Preferably, homologous recombination takes place during DNA replication or mitosis of the cells. A DNA of this kind can be used for the production of an agent for therapeutic treatment of tumors or for the production of homologous or heterologous LST-1 protein in a host organism.

It is possible to provide a test on the basis of the nucleic acid sequences of the LST-1 protein provided by the invention which can be used to detect nucleic acids which code for LST-1 proteins. Such a test can for example be carried out in cells or cell lysates and by means of nucleic acid diagnostics. In this case the sample to be examined is brought into contact with a probe which would hybridize with the nucleic acid sequence coding for the LST-1 protein A hybridization between the probe and nucleic acids from the sample indicates the presence of expressed LST-1 proteins. Such methods are known to a person skilled in the art and are for example described in WO 89/06698, EP-A 0 200 362, U.S. Pat. No. 2,915,082, EP-A 0 063 879, EP-A 0 173 251, EP-A 0 128 018. In a preferred embodiment of the invention, the nucleic acid of the sample which codes for a LST-1 protein is amplified before testing, e.g. by the well-known PCR technique. A derivatized (labelled) nucleic acid probe is usually used in the field of nucleic acid diagnostics. This probe is brought into contact with a carrier-bound denatured DNA or RNA from the sample and in this process the temperature, ionic strength, pH value and other buffer conditions are selected in such a way that—depending on the length of the nucleic acid sample and the resulting melting temperature of the expected hybrid—the labelled DNA or RNA can bind to homologous DNA or RNA (hybridization, see also Southern, E. M., J. Mol. Biol. 98 (1975), 503–517; Wahl, G. M. et al., Proc. Natl. Acad. Sci. USA 76 (1979), 3683–3687). Suitable carriers are membranes or carriers materials based on nitrocellulose (e.g. Schleicher and Sch üll, BA 85, Amersham Hybond, C.), reinforced or bound nitrocellulose in a powder form or nylon membranes derivatized with various functional groups (e.g. nitro group) (e.g. Schleicher and Schüll, Nytran; NEN, Gene Screen; Amersham Hybond M; Pall Biodyne).

The hybridized DNA or RNA is then detected by incubating the carrier, after thorough washing and saturation to prevent unspecific binding, with an antibody or antibody fragment. The antibody or antibody fragment is directed towards the substance incorporated into the nucleic acid probe during the derivatization. The antibody is in turn labelled. It is, however, also possible to use a directly labelled DNA After incubation with the antibodies, it is washed again in order to only detect specifically bound antibody conjugates. The determination is then carried out via the label of the antibody or antibody fragment according to well-known methods.

The detection of the LST-1 expression can be carried out for example as:

- in situ hybridization with immobilized whole cells using immobilized tissue smears and isolated metaphase chromosomes,
- colony hybridization (cells) and plaque hybridization (phages and viruses),
- Northern hybridization (RNA detection),
- serum analysis (e.g. cell type analysis of cells in serum by slot-blot analysis),
- after amplification (e.g. PCR technique).

The invention therefore includes a method for the detection of nucleic acids which code for a LST-1 protein which is characterized in that the sample to be examined is incubated with a nucleic acid probe which is selected from the group comprising a) the DNA sequences shown in SEQ ID NOS:1 and 2 or a complementary sequence to these, b) nucleic acids which hybridize under stringent conditions with one of the sequences from a), the nucleic acid probe is incubated with the nucleic acid from the sample and the hybridization of the nucleic acid in the sample and nucleic acid probe is detected, if desired, via a further binding partner.

Thus, LST-1 is a valuable prognostic marker in tumor diagnostics (metastasis, progress) and an activity marker for cell proliferation, especially for T cell leukemic cells.

The human histiocytic lymphoma cell line U-937 was accorded the deposit number DSM ACC 5 and has since Apr. 3, 1990 been contained in, and freely accessible at, the public collection of Deutsche Samnlung von Mikroorganismen und Zeilkulturen GmbH, Mascheroder Weg 1b , D-38124 Braunschweig.

Plasmid pLST-1 which contains the LST-1 gene was deposited by Boehringer Mannheim GmbH at the Deutsche Sammlung von Mikroorganismen und Zeilkulturen GmbH, Mascheroder Weg 1b, D-38124 Braunschweig on May 24, 1995 and assigned the number DSM 10011.

The invention is elucidated in more detail by the sequence listing in conjunction with the following examples. In this case SEQ ID NO 1 denotes the nucleotide sequence of the LST-1 genomic region. A polymorphic Pvu II restriction site is at position 2841. The TATA box, the IFN-γ-activated site (FcγR1), and the interferon-stimulated gene factor-2 responsive element (ISGF-2) are starting at positions 279, 1509, and 1814, respectively. The DNA sequence has been submitted to Gen-Bank databank (accession number U00921).

SEQ ID NO 2 denotes protein and cDNA of LST-1.

SEQ ID NO 3 denotes LST-1 protein sequence (104 amino acids).

SEQ ID NO 4 denotes LST-1 protein sequence (isoform 97 amino acids) Abbreviations: BAT, HLA-B-associated transcript; MHC, major histocompatibility complex LST-1, Leucocyte Specific Transcript-1; pLst1, LST-1 cDNA clone; MER, medium reiteration frequency repeat; TNF-α; tumor necrosis factor-α; TNFA, gene coding for TNF-α; TNFB, gene coding for tumor necrosis factor-β; LTB, gene coding for lymphotoxin-β.

EXAMPLE 1

Isolation of the LST-1 Genomic Region

The human B cell line CAH was established from a homozygous individual typed HLA-A3, −Bw47, −Cw6, and −DR7. Genonic DNA was used to generate the cosmid library cah in the vector pTCF as described previously (E. H. Weiss et al., Immunobiology 170 (1985) 367–380). Several cosmids were isolated by hybridization to a TNFA probe. A subclone derived from the cosmid cah5 containing the region upstream of the LTB gene was obtained by Hind III endonuclease restriction of cah5. Religation of the digest resulted in a truncated clone (cah5dH3) of 18 kb length. Five adjacent Pst I fragments of 1.5 kb, 0.8 kb, 3.1 kb, 0.4 kb and 0.7 kb referred to as Pst6, Pst4, and Pst11, Pst400 and Pst700 respectively, were isolated and subcloned into the vector pUC19.

EXAMPLE 2

Determination of the Nucleotide Sequence

The subclones Pst4, Pst6, and Pst11 and two additional 5' PstI fragments of 400 and 700 bp respectively (Pst400 and Pst700) were sequenced in both directions with the dideoxy-nucleotide chain termination method using either Sequenase 2.0 (USB, Braunschweig, Germany) or T7 polymerase (Pharmacia, Freiburg, Germany). The genomic organization of these fragments was determined by direct sequencing of cah5dH3 across the Pst I restriction sites, employing oligo-nucleotides. This confirmed the order and excluded the possibility that any small fragment is situated between the restriction fragments Pst6, Pst4, Pst11, Pst400 and Pst700.

EXAMPLE 3

Cell Culture and Stimulation Experiments

Non-adherent human Jurkat T cells, the human histiocytic cell line U-937, and the human monocytic cell line Mono-Mac6 were grown in RPMI 1640 medium. The adherent A431 and HeLa epithelial carcinoma lines were grown in Dulbecco's modified Eagle's medium (DMEM. For both media 10% heat inactivated fetal calf serum, 1% penicillin/streptomycin and 1% L-glutamine (all purchased from Gibco-BRL, Berlin, Germany) were used as a supplement. All cells were cultured at 5% $CO_2$ and 37° C. in a humidified atmosphere. Stimulation of Jurkat cells was carried out with 50 ng/ml 12-O-tetradecanoylphorbol-13-acetate (TA) (Sigma, Deisenhofen, Germany) and 5 μg/ml phytohemag-glutinin (PHA) (Sigma). The human monocytic cell line MonoMac6 was stimulated with 1 mg/ml lipopolysaccha-rides (prepared from Salmonella minnesota; Sigma) for 4 hours. The histiocytic cell fine U-937 was stimulated with 200 U/ml interferon-γ for 48 hours.

EXAMPLE 4

Cloning, Characterization and Expression of the LST-1 cDNA

Reverse transcription of RNA, followed by the polymerase chain reaction (RT-PCR) of mRNA isolated from U-937 cells stated with interferon-γ, resulted in a cDNA clone, designated pLst1 of 636 bp length. This is in good agreement with the size of mRNA detected by Northern blot of about 800 bp length, due to an expected length of the poly(A) tail of about 200 bp. The cDNA sequence of pLst1 was identical to the coding regions of the genomic sequence cloned from a different human cell line. Sequence analysis revealed three regions which are well conserved between the human LST-1 and the mouse B144 transcript, and could be assigned to exon 2–4 of the human gene.

Like the other genes in the TNF region, LST-1 consists of six exons (1A, 1B, 2, 3, 4, 5) and five introns. Its transcription orientation is the same as for TNFA and TNFB, but opposite to the neighboured LTB gene. This result does not agree with the orientation of the mouse B144 gene as marked in the organization of the H-2D$^b$ region an published by J. M Wroblewski et al., Immunogenetics 32 (1990) 200–204. The human pLs 1 cDNA clone contains an extended 5' region encoding stop codons in all three reading frames and can therefore be considered to be full length. The LST-1 cDNA potentially encodes a transmembrane protein The LST-1 cDNA can be expressed in prokaryotes, preferably in E.coli, using an appropriate vector (e.g. pBR 322). The protein can be isolated either after secretion or from cytoplasmatic accumulated inclusion bodies and subsequent naturation.

EXAMPLE 5

Expression of LST-1

LST-1 mRNA is expressed constitutively in T cells, macrophages, U-937, and at low levels in human tonsilla, lung, and liver, which may be due to lymphocytes and macrophages present in these tissues. In epithelial cell lines such as HeLa and A431 cells, no LST-1 transcripts were detectable (data not shown). This expression pattern prompted us to name the corresponding gene Leucocyte Specific Transcript-1 (LST-1). Transcription levels can be strongly enhanced in U-937 cells by stimulation with interferon-γ, but not by lipopolysaccharides in the macrophage cell line MonoMac6. Stimulation of the Jurkat T cell line with TPA (12-O-tetradecanoylphorbol-13-acetate) induced transient expression of LST-1 mRNA above the constitutive level. Following induction, the mRNA expression level increased after 4 hours with a peak at 8 hours and decreased after 24 hours of stimulation.

LIST OF REFERENCES

Ausubel, I., Frederick, M., Current Protocols in Mol. Biol. (1992), John Wiley and Sons, New York
Büttner et al., Mol. Cell Biol. 11 (1991) 3573–3583
Doetschman et al., Nature 330 (1987) 576–578
Doetschman et al., Proc. Natl. Acad. Sci. USA 85 (1988) 8583–8587
EP-A 0 173 251
EP-A 0 063 879
EP-A 0 128 018
EP-A 0 200 362
Feigner et al., Proc. Natl. Acad. Sci. USA 84 (1987) 7413
Friedmann, T., Science 244 (1989) 1275; Morgan 1993, RAC DATA MANAGEMENT REPORT, June 1993
Hames, B. D ., Higgins, S. G., Nucleic acid hybridisation—a practical approach (1985) IRL Press, Oxford, England
Harlow and Lane eds., Antibodies: A laboratory manual (1988), Cold Spring Harbor Laboratories Press
Köhler and Milstein, Nature 256 (1975) 495–497
Kucherlapati, Proc. in Nucl. Acids Res. and Mol. Biol. 36 (1989) 301
Margolskee et al., Mol. Cell. Biol. 8 (1988) 2937
McLughlin, J. Virol. 62 (1988), 1963
Miyajima, A., et al., Annual Reviews Immunol. 10 (1992) 295–331
Moss et al., Ann. Rev. Immunol. 5 (1987) 305
Mulligan, R. C. (1991) in Nobel Symposium 8: Etiology of human disease at the DNA level (Lindsten, J. and Pattersun Editors) 143–189, Raven Press
Rasmussen et al., Methods Enzymol. 139 (1987) 642
Sambrook, J., et al., "Expression of cloned genes in E. coli" in Molecular Cloning: A laboratory manual (1989) Cold Spring Harbor Laboratory Press, New York, USA, 9.47–9.62 and 11.45–11.61
Southern, E. M., J. Mol. Biol. 98 (1975), 503
Thomas and Capecchi, Cell 51 (1987) 503–512
Thomas et al., Cell 44 (1986) 419–428
Thompson, A., ed. (1991), The Cytokine Handbook, London, Academic Press
U.S. Pat. No. 2,915,082
Wahl, G. M et al., Proc. Natl. Acad. Sci. USA 76 (1979), 3683–3687
Weiss, E. H., et al., Immunobiology 170 (1985) 367–380
WO 89/106698
Wroblewski J. M., et al., Immunogenetics 32 (1990) 200–204

What is claimed is:

1. A DNA molecule comprising the sequence shown in SEQ ID NO:2.

2. A process for the recombinant production of a protein which binds on the surface of leukocytes, comprising
   - inserting a DNA according to claim 1 into a suitable host cell,
   - culturing said host cell containing the DNA in a culture media to obtain expression of said protein, and
   - isolating said protein from said host cell or said culture media.

3. A recombinant expression vector comprising the DNA molecule of claim 1.

4. A prokaryotic or eukaryotic host cell which is transfected with a vector according to claim 3, wherein said host cell is capable of producing said protein.

5. The host cell according to claim 4, wherein said host cell is an *E.coli* or a mammalian cell.

6. Plasmid DSM 10011.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 5581 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: exon
      (B) LOCATION:48..162

(ix) FEATURE:
    (A) NAME/KEY: exon
    (B) LOCATION:544..652

(ix) FEATURE:
    (A) NAME/KEY: exon
    (B) LOCATION:1044..1162

(ix) FEATURE:
    (A) NAME/KEY: exon
    (B) LOCATION:1475..1567

(ix) FEATURE:
    (A) NAME/KEY: exon
    (B) LOCATION:1775..1797

(ix) FEATURE:
    (A) NAME/KEY: exon
    (B) LOCATION:2325..2709

(xi) SEQUENCE DESCRIPTION: SEQ ID NO: 1:

```
GAGCCGAACT TCCTCTCCTA CAATGCTGG GGAGGAACCC AGCCTGGGGG AGAAGTTAAA      60
GCCAGAGGAG GGGCAGGAAT GTCTGAGGTG CAACACTTC TCTTCAGCCA GACAGCACTG     120
GCCAGTTTGG AGTCTGTCCA TCCTGCAGGC CACAAGCTCT GGGTAAGCTG GAATGGGCA     180
GGGACCTTGG TGGAAGGATG GTCACACCCC AGAGTGGGGT GAAGCTAAGA TGAGGGGAGG    240
GAGAGTATGG GTTTGAGTTT CCCTGGGCCG TCGAGGAATC CTCTGAGTCT CTGCTCCCCA    300
AAGAAATTAA AGACAATTCA TTTCTGTGCC CACGGCCCTT ATGGCTCCAC CTGCACTTCT    360
GCTCCCCACC CCCCAGAATT CCTCTTAAAC CCAGAAGGTC CCAGTTTCCA GACCCTAGTC    420
AGTATATCTG GCTCTGGGGT GAAGAGAACG GCCCCCTCTT CACCCTCAAA CAGGAACCAG    480
TGGTTGGAGG GGAGGAAGTG CCTGAGGGGA AGTTATGGGG CCCCAGATAC TCCTCCATGC    540
CCCACTTCAG CCCTAGCAGC ATCTGCCTGT GGGAAGCAGC TCTCCACACC AGCCAAGGGG    600
GCCCCCACAC TCCCGCGCTG CTCTGCGGCT CAGGGAGCAG CCCACCTGCT GGGTGTGCTG    660
ATATCACCCT CCCTTCTTCC CCCCAGTGCC CACACCCACC CAGGCCCAGG CTCCTTCCCC    720
TCCATCATCC CCTTACCAGC ACCTAGAACC ATCCAGGGCT GAAAAGTCCC CTCCAAACCA    780
CGTGGTCAGC CCAGGGCAGA GGAAAGGGCT GGGCTCTGGA GTTGGGCAGA GCTGGCCTTA    840
AACCCCAGCT CCACCTTTCT GGGATGGGTG ACCTAGTAAA GTCCAGGCTT GAATCTCGGG    900
TCTTTACTTG GCAACGGGC ACCATGGATAC CCTATGTTCT GGGGATTAGC AGTGAGGAAT    960
GGAAAGTGCC CAGCTCGGGT TGGCACATAA GGGAGGCTCC CCAGCCTGGG AACGATTATA   1020
ACAGAGGGCC CCTCACTTCA CAGATGAGGA ACTTGAGGCA AGTCACCAGC CCCTGATCAT   1080
TTCGCCTAAA AGAGCAAGGA CTAGAGTTCC TGACCTCCAG GCCAGTCCCT GATCCCTGAC   1140
CTAATGTTAT CGCGGAATGA TGGTAAGTAA AGTGTCTCTT GCATCTGCAT AGAGAGAGTC   1200
CTGGGAGCTT AGGAAGTGAT GGGGAACAGT GATGTATGCA GCTTGGACAG GCCTCTGGGG   1260
ACAGCTGGTA CAGGAGGGAA AGGGACCTCA CGGGAGGCCC AGAAACCTGG TAAGAGGTGA   1320
GGTATTAAGG TCTGGGATGG AGAAGCTCTG AGGGTATATT TTTCTGCCTC TAAAACTGTT   1380
GGAGAGGGAA TCTGAGAAAG CTGCAACCAA CCAGGAGGCT GGGGTACGCT GGAGAAGGAA   1440
TGGGCTTCCT AACCTTGAGC CCTCTTCCCT GAAGATATAT GTATCTACGG GGGCCTGGGG   1500
CTGGGCGGGC TCCTGCTTCT GGCAGTGGTC CTTCTGTCCG CCTGCCTGTG TTGGCTGCAT   1560
CGAAGAGGTG AGCGCTGCAC TCCCTCCCTC CCCCTGCAGC AGTGCCCCCT GTGCCCCCAC   1620
CCCCACACGC TTTCCCACTG CTTTCCCAGA ACACTGCCTG GCCCTGGAGC CACTGGGAAG   1680
```

-continued

```
CCAACAGGGG AGTCCACGCC TGCTGGTGGG GGGAGCCCGG GAGGCGGGAG AAGCACAAAG    1740

GGTGGGCTGT GTTGAGCTTC TTCTTTTCTT CCAGTAAAGA GGCTGGAGAG GAGCTGGGTG    1800

AGTCTGGGGA CAGGGAAGGG GGAGGGCAAG AGAGATCCTG AGTGGGTGAG TGGGGAGAAG    1860

CATGGCTGAG CGCTGAGAGG AGGGTTGGGG ACGGGAGACA AGGAGAGAGA AAGTAGGAGC    1920

ATGAGAGAGG CAGAGAAAAT CGAGGCAAAA GAGAAAGAGA AAATGAGACA GAAACCAAGA    1980

GAAAAGTGA GACAGAGGAT AGGAGAGACA GGGAGAAAAT GAGAGTGAGA GAGACACAAA     2040

GAGAAGAGCA ATGAAAGAGA GAGAGAGAGA GAGGCTCCAG AACCAGGCAC AGTGGCTCAC    2100

GTCTGTCATT CCACTATCGC AAGGCTGAGG CAGGAAGATA GCTTGAGCTC AGGGGTTGAA    2160

GACAATCCTG GACAACATAG TGGACTCTGT CTCCAAAGAA AAAAGAGAGA GAGAGAGAGA    2220

GAGAGAGAGA GGGAGAGAGA GAGAGAGAGA GGGAGAGAAG TAAGAAAGGC TGGAGGTGGG    2280

AGCAGAACTC ACAGGGAAGG ATCTGACGCA TCGCCTCCCA TCAGCACCTT CTGTCCTGGT    2340

CCCAGGCCCA GGGCTCCTCA GAGCAGGAAC TCCACTATGC ATCTCTGCAG AGGCTGCCAG    2400

TGCCCAGCAG TGAGGGACCT GACCTCAGGG GCAGAGACAA GAGAGGCACC AAGGAGGATC    2460

CAAGAGCTGA CTATGCCTGC ATTGCTGAGA ACAAACCCAC CTGAGCACCC CAGACACCTT    2520

CCTCAACCCA GGCGGGTGGA CAGGGTCCCC CTGTGGTCCA GCCAGTAAAA ACCATGGTCC    2580

CCCCACTTCT GTGTCTCAGT CCTCTCAGTC CATCTCGAGC CTCCGTTCAA ATTGATCATC    2640

ATCAAAACTT ATGTGGCTTT TTGACCTTTG AATAGGGAAT TTTTTAAATT TTTTAAAAAT    2700

TAAAATAAAA AAAACACATG GCTCACCCTT CCACCCACTC TGGGGTCAAA TAGTAATTTG    2760

TTGGGTGAAT GACAGTGTTC AGGGACCCAA GCTCCCCTAA CAGCCAGAAG AGGGTATGTG    2820

TGGGCCTGGC AGGAAAGGGC AGTTGCCAAG GAGGAGTCAT ATCTGATCCT TCCCATTTCT    2880

CAGGACAATC AGGCTCAGCC TCCTGGGACT GGGGGAAGCA GATGTGCTGA GCTCCCACAT    2940

GGTGGTGGGA GGGGCGCTGG GACCACAGCC GGCAGCTGCC TTCTTGGACC TTTCCAGGTC    3000

AGACCTGGTG GAAGGGAAAG TTCAGAGTTG GGGGAATCCG GAGAGAGTAG ATTTGGCATC    3060

TGGAGAATGG AGAAGAAAAC ACTTGAGACT CATGAGGAGT TAGTGGTGGG GCAGATTTAT    3120

TGGGGTCTTT TGAAGAGGAC TAGGGACATC TGGGCTCTGG AATCACTCCT CGGGGCCCAT    3180

CTGAGGAGTG GCAGTGTGTT CCCATGTGAC AGTGGCCTGG TCAGAGAGAG GACAGGAGCT    3240

GCTCAGTGTT GCAGTCCCGA GGCTCTCCTC TTCCTGGTCT CTGTCCTCCC TCCTCCCACT    3300

CTCTTACTGC CCCTCCCATC CCGTCCACTA TTGCCCCTGG CTCCATTACT CACATTTGCC    3360

CTGGTAATAG ACGGTGCTGC CCACGGCCAC AGAGAGAAAG CTGACAGCAT AGAATCCAGC    3420

CCGAAGAGGA GGACTGTACC AGCCCCCTAG CTGAGGATGT TCTGCATGGG GCAATGGAGA    3480

CGGGGGTTGG GGAAGAAGTG CACACAGGCT CAGGGAGGGA AGGGCCTCA GAGGAGCATC     3540

CCTGCCTCCC AAGGACATTG CCTCTTGGGC CTCCAGCCAG GAGGAGACAC CACCTCCCAG    3600

CATCTCACCT TTCTCCACCA CCAGCCGAGT CCCATTCCCT GTCCCGACAC CAAGGCCCAG    3660

CACCTCCACT CTGCACACGT AGATGCCTGG CGTCATGGCC TCGCACGTCC CGGATGTGCA    3720

GCTCAGCCTG GTGGTCATGG AGGAAACGGG AAGAAGCAGA TGGAGGCGGC CCCTGAACTC    3780

TGGGGTTCCA TTCCTCACCT CCTTCCCTGG AACCACCTCA TCTCGGAACC ACGTGACGGA    3840

GCCAATGGCC AGTCTCCCTT GGCTGGCATT GAAGGAGCAG GGCAGGAAGG CAGAGGATCC    3900

TTCCAGGGTA CGAATCTCAG GGGGCTGGGA CACCCAGAGA GCACAGGAAT CCTGGGGGGA    3960

AAAGGGAGAC CCAGAGAAAC ACCTCCCCAG TTATTCCAAA GAGAAAAGAC AACAGAGCTT    4020

GGAGTAGAAC ATCCCAGCTT TCTCCAGGCA TAGGGTGCAT GGGAATAGAT ACTTTGGGGC    4080
```

```
CTCATTAAAC CCTTCCCTCT TAACCAATCT GATTTCTTAA CATTGCTTAT TAAATCATTT      4140

TTCGGCTGGG TGCAGTCGCA CGCCTGTAAT CCCAGCACTT TGGGAGGCCG AGGTGGGCGG      4200

ATCACCAGGT CAGGAGATCG AGACCATCCT GGCCAACATG GTGAAACCCC GTCTCTACTA      4260

AAAAAATACA AAAATTAGCC GGGCATGGTG GTGTGCACCT GTAATCCCAG CTACTCGGGA      4320

GGCTGAGGCA GGAGAATCGC TTGAACCCGG GAGGCAGAGG TTGCAGTGAG CCAAGATTGC      4380

GCCATTGCAC TCCAGCCTGG GCGACAAAGC AAGACTCCAT CTCAAAAAAT AAAAAATAAA      4440

AATCATTTTT CAAATTCTTC CTATACCAAC TCTCACTCTC ACCCTCTGCC ATCATTCTCC      4500

AGCCAGTTCA GTAGTAACTT GTCTAGCTGA AATGTAAACC ATCATGGTGA AATTAAGCTC      4560

ATTAATGAAT TGCAGCTGCC TAGTTAACTA ATATCACTCA TTATATTATG CAGGTATTAT      4620

TTTAGTACAA ATGGCATTGT ACAGTAAGCC ATCCTTCCTC TTTTTCTTTT TTCTTTTTTT      4680

GAGATGGGGT CTTGCTCTGT TGCCCAGGCT GGAATGCAGT GGTGCAATCT TGGCTCACTG      4740

CAAACTCCGT CCCCTGGGTT CAAGCGATCC TGGTGCCTCA GCCTCCCAAG TAGCTGGGAC      4800

TACAGGCACC CACCACCACG ACTGGCTAAT TTTTGTATTT TCAGTCGAGA CAGGGTTTCC      4860

ACCATCTGGT CTCAAACTCC TGACCTCAAG TGATCCACCC ACCTCGGACC AGGCTGGCTC      4920

AAACTCCTGA TCTCAAGTGA TCCACCTGCC TCGGCCTCCC AAAGTGCCAC CCAGCCACTC      4980

TTGGTTTTCG TTAAAGAAAG TAACTAATTA AATCTCCAGG TGAAGACGTG GCCTTAATTG      5040

GTTGAGATTC CTATTTAACC CGTCCATGTT GATGAATTAA ACCAAATATT AAAATCCCTG      5100

ATTAAATTAT CTACTTAGGG AAATTTACAA GTCATTCTAT TTCAGTGGTT CTCAAACTTG      5160

AGTGTGTATG GAAATTACCT GGAGCATCTG CTAGAACAGA TTCCTGGGCC TACCCCCCGA      5220

GTTTTTGACT CAGTAGGTCT GGAGTGGGGC CTAAGAATTT GTTCTAGGTT CCCAGAAATC      5280

CACATTTTGA GAACTCCTGC ATTTAGTTAA TAATATGCCT GATAGTTAAG GTCTCTCAGT      5340

TCATTAAAAA CAGTTTCGGC CGGGTGCAGT TCGCACGCCT ATAATCCCAA CACTTTGGGA      5400

GGCCAAGGCG AGTGGATCAC CTGAGGTCAG GAGTTTGAGA CCAGCCTGGC CAACATGGTG      5460

AAACCTCGTC TCTACTAAAA ATACACAAGT TAGCCAGCAG TAATGGCATG CACCTGTAAT      5520

CCTAGCTACT TGGGAGGCTG AGACAGGAGA ATCATTTTTA CCCAGGAGGT GGAGGCTGCA      5580

G                                                                    5581
```

(2) INFORMATION FOR SEQ ID NO: 2:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION:1..312

(xi) SEQUENCE DESCRIPTION: SEQ ID NO: 2:

```
ATG TTA TCG CGG AAT GAT GAT ATA TGT ATC TAC GGG GGC CTG GGG CTG        48
Met Leu Ser Arg Asn Asp Asp Ile Cys Ile Tyr Gly Gly Leu Gly Leu
 1               5                  10                  15

GGC GGG CTC CTG CTT CTG GCA GTG GTC CTT CTG TCC GCC TGC CTG TGT        96
Gly Gly Leu Leu Leu Leu Ala Val Val Leu Leu Ser Ala Cys Leu Cys
            20                  25                  30

TGG CTG CAT CGA AGA GTA AAG AGG CTG GAG AGG AGC TGG CAC CTT CTG       144
```

```
                   Trp Leu His Arg Arg Val Lys Arg Leu Glu Arg Ser Trp His Leu Leu
                            35                  40                  45

TCC TGG TCC CAG GCC CAG GGC TCC TCA GAG CAG GAA CTC CAC TAT GCA                    192
Ser Trp Ser Gln Ala Gln Gly Ser Ser Glu Gln Glu Leu His Tyr Ala
     50                  55                  60

TCT CTG CAG AGG CTG CCA GTG CCC AGC AGT GAG GGA CCT GAC CTC AGG                    240
Ser Leu Gln Arg Leu Pro Val Pro Ser Ser Glu Gly Pro Asp Leu Arg
 65                  70                  75                  80

GGC AGA GAC AAG AGA GGC ACC AAG GAG GAT CCA AGA GCT GAC TAT GCC                    288
Gly Arg Asp Lys Arg Gly Thr Lys Glu Asp Pro Arg Ala Asp Tyr Ala
                     85                  90                  95

TGC ATT GCT GAG AAC AAA CCC ACC                                                    312
Cys Ile Ala Glu Asn Lys Pro Thr
                100
```

(2) INFORMATION FOR SEQ ID NO: 3:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO: 3:

```
Met Leu Ser Arg Asn Asp Asp Ile Cys Ile Tyr Gly Gly Leu Gly Leu
 1               5                  10                  15

Gly Gly Leu Leu Leu Leu Ala Val Val Leu Leu Ser Ala Cys Leu Cys
                 20                  25                  30

Trp Leu His Arg Arg Val Lys Arg Leu Glu Arg Ser Trp His Leu Leu
             35                  40                  45

Ser Trp Ser Gln Ala Gln Gly Ser Ser Glu Gln Glu Leu His Tyr Ala
     50                  55                  60

Ser Leu Gln Arg Leu Pro Val Pro Ser Ser Glu Gly Pro Asp Leu Arg
 65                  70                  75                  80

Gly Arg Asp Lys Arg Gly Thr Lys Glu Asp Pro Arg Ala Asp Tyr Ala
                     85                  90                  95

Cys Ile Ala Glu Asn Lys Pro Thr
                100
```

(2) INFORMATION FOR SEQ ID NO: 4:

(i) SEQUENCE CHARACTERISTICS:
        (A) LENGTH: 97 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 4:

```
Met Leu Ser Arg Asn Asp Asp Ile Cys Ile Tyr Gly Gly Leu Gly Leu
 1               5                  10                  15

Gly Gly Leu Leu Leu Leu Ala Val Val Leu Leu Ser Ala Cys Leu Cys
                 20                  25                  30

Trp Leu His Arg Arg Val Lys Arg Leu Glu Arg Ser Trp Ala Gln Gly
             35                  40                  45

Ser Ser Glu Gln Glu Leu His Tyr Ala Ser Leu Gln Arg Leu Pro Val
     50                  55                  60

Pro Ser Ser Glu Gly Pro Asp Leu Arg Gly Arg Asp Lys Arg Gly Thr
 65                  70                  75                  80
```

```
-continued

Lys Glu Asp Pro Arg Ala Asp Tyr Ala Cys Ile Ala Glu Asn Lys Pro
                85                  90                  95
Thr
```